United States Patent [19]

Chu et al.

[11] Patent Number: 4,879,248
[45] Date of Patent: Nov. 7, 1989

[54] ASSAY FOR TRICHOTHECENES

[75] Inventors: Fun S. Chu; Ru-Dong Wei; Guang S. Zhang, all of Madison, Wis.

[73] Assignee: Wisconsin Alumni Research Foundation, Madison, Wis.

[21] Appl. No.: 43,648

[22] Filed: Apr. 28, 1987

[51] Int. Cl.$^4$ .................. G01N 33/531; G01N 33/543; G01N 33/537; B63H 1/08

[52] U.S. Cl. ..................................... 436/543; 436/93; 436/518; 436/538; 436/544; 436/815; 436/822; 436/825

[58] Field of Search ........................... 435/7, 188, 810; 436/518, 538, 539, 544, 545, 546, 93, 800, 804, 805, 808, 815, 822, 825, 543

[56] References Cited

PUBLICATIONS

Xu et al., J. Assoc. Off. Anal. Chem. 69(6), 967–969 (1986).
Zhang et al., J. of Food Protection 49(5), 336–339 (1986).
H. Kemp et al., 37 J. Sci. Food Agric., 888–894 (1986).
T. Fan et al., 47 J. Food Prot., 964–967 (1984).
J. Pestka et al., 940A–944A, JAOCS (1981).
S. Lee et al., 72 Tox. Appl. Pharm. 228–235 (1984).
F. Chu et al., 37 Appl. Environ. Micro., 104–108 (1979).
G. Zhang et al., 51 Appl. Environ. Micro., 132–137 (1986).
R. Wei et al., 49 J. Food Prot. 267–271 (1986).
F. Chu et al., 48 Appl. Environ. Micro., 781–784 (1984).
R. Vesonder et al., 16 Process Biochem., 12–15 (1980).
G. Bennett et al., 58 J. Am. Oil Chem. Soc. 1002A–1005A (1981).
K. Ehrlich et al., 48 Microbiology, 1053–1054 (1984).
F. Chu et al., 48 Appl. Environ. Micro., 777–780 (1984).
F. Chu, Mycotoxins and Phycotoxins, P. S. Steyn and R. Vleggar, (Eds) 277–292 (1985).
F. Chu, 47 J. Food Prot., 562–569 (1984).
Yoshizawa et al., 46 Agric. Biol. Chem., 2613–2615 (1982).
Wei et al., 45 Biochem. Biophys. Res. Comm., 396–401 (1971).
Wallace et al., 25 J. Ag. Fd. Chem., 836–838 (1977).
R. Wei et al., 160 Anal. Biochem., 399–408 (1987).
T. Fan et al., 53 Appl. Environ. Micro., 17–21 (1987).

Primary Examiner—Robert J. Warden
Assistant Examiner—Jack Spiegel
Attorney, Agent, or Firm—Quarles & Brady

[57] ABSTRACT

An immunoassay for trichothecenes that have at least three hydroxyl groups at specified positions is disclosed. It relies on developing antibodies to close trichothecene variants that are missing at least one of the hydroxyl groups, and then using these antibodies to test specimens in which the trichothecene has been converted to the variant (usually to the OAC variant). For example, DON and T-2 tetraol can be assayed for using this invention.

7 Claims, 2 Drawing Sheets

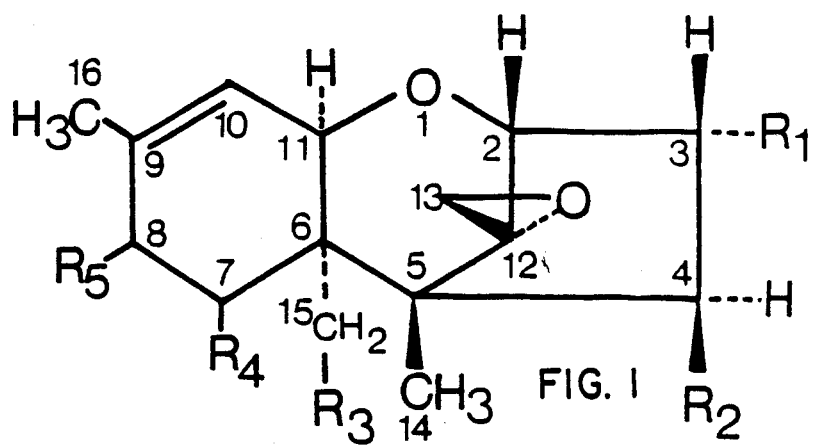

FIG. 1

| NAME | SIDE CHAIN RESIDUE AT POSITION: | | | | |
|---|---|---|---|---|---|
| | $R_1$ | $R_2$ | $R_3$ | $R_4$ | $R_5$ |
| Acetyl-DON | OAc | H | OAc | OAc | =O |
| Acetyl-T-2 | OAc | OAc | OAc | H | ISV |
| CMO-DAS | CMO | OAc | OAc | H | H |
| CMO-T-2 | CMO | OAc | OAc | H | ISV |
| DAS | OH | OAc | OAc | H | H |
| DON | OH | H | OH | OH | =O |
| DOVE | H | H | OH | H | H |
| H-T-2 | OH | OH | OAc | H | ISV |
| 4-MAS | OH | OAc | OH | H | H |
| 15-MAS | OH | OH | OAc | H | H |
| NEOS | OH | OAc | OAc | H | OH |
| 3'OH-T-2 | OH | OAc | OAc | H | OH-ISV |
| T-2 | OH | OAc | OAc | H | ISV |
| T-2 tetraol | OH | OH | OH | H | OH |
| T-2-TA | OAc | OAc | OAc | H | OAc |
| Tri-Ac-DON | OAc | H | OAc | OAc | =O |
| 15-Ac-DON | OH | H | OAc | OH | =O |
| Nivalenol | OH | OH | OH | OH | =O |
| DHC | OAc | H | OAc | OH | OH |

ASSAY FOR TRICHOTHECENES

This invention was made with United States Government support awarded by the Department of Defense, Grant Number DAMD-82-2021. The United States Government may have certain rights in this invention.

This invention relates to an assay for testing for the presence of certain trichothecenes. The invention involves the use of immunoassay techniques in testing for trichothecenes that have at least three hydroxyl groups in specified ring positions.

BACKGROUND OF THE INVENTION

Naturally occurring trichothecenes are a group of toxic secondary fungal metabolites which are produced by a number of fungi in the general Fusarium, Trichoderma, Myrothecium and Stachybotrys. Some natural and some man made examples of trichothecenes are described in FIGS. 1 and 2. As shown in FIG. 1 of the attached drawings, trichothecenes contain a common skeleton with different side chain residues at points $R_1$–$R_5$. Three typical classes of natural trichothecenes are type "A" (where $R_5$ is H or ISV), type "B" where $R_5$ is =O, and type "C" where $R_2$ is linked to $R_3$ by a carbon chain.

Because of their toxic effects and the frequent contamination of these toxins in foods and feeds, trichothecenes are potentially hazardous to human and animal health. There is also concern regarding the possible use of these compounds as biological warfare compounds (e.g. in "yellow rain"). A dependable, sensitive, specific, simple, and inexpensive method for the detection of mycotoxins in foods, feeds, and biological fluids is therefore highly desirable. Testing for trichothecenes has in the past been extremely difficult because this group of mycotoxins does not possess a chromophore group. Methods such as thin-layer chromatography, gas liquid chromatography, and mass spectrometry, which have been used for analysis of this group of mycotoxins are lacking in sensitivity and/or specificity, or need expensive instruments. Also, extensive cleanup is generally necessary before actual analysis.

To overcome some of the difficulties encountered with these prior assay methods, attempts have been made to develop immunoassays for trichothecenes by utilizing the principle of specific antigen-antibody interaction. However, trichothecenes are small molecular weight organic compounds which are too small to lead to desired levels of antibody development. Thus, they must first be conjugated to a protein or a polypeptide carrier in order for antibodies to be developed to them. Since natural trichothecenes do not have a reactive group that can be directly conjugated to protein, it is necessary to first introduce a reactive group before the coupling reaction takes place. Approaches which have been used for conjugation involve the introduction of various reactive groups at $R_1$ and $R_5$.

Such studies have led to the development of specific antibodies against T-2, DAS, and DOVE. See FIG. 2 and F. Chu et al., 37 Appl. Environ. Microbiol. 104–108 (1979); G. Zhang et al., 51 Appl. Environ. Microbiol. 132–137 (1986); R. Wei et al., 49 J. Fd. Prot. 267–271 (1986); F. Chu et al., 48 Appl. Environ. Microbiol. 777–80, 781–84 (1984). The disclosure of these articles and all other articles recited herein are incorporated herein by reference as if fully set forth herein.

This approach has problems for trichothecenes such as DON, T-2 tetraol, and nivalenol. This is due to the presence of many hydroxyl groups at the $R_1$–$R_5$ positions. Such groups not only create problems in conjugation to proteins, but also appear to render the molecule less immunogenic (or may produce antibodies that are currently undetectable).

Thus, it can be seen that a need exists for an improved immunoassay for trichothecenes which are of the type where at least three of the $R_1$–$R_5$ moieties are OH groups.

Summary Of The Invention

In one aspect, the invention provides an assay for the presence in a sample of a trichothecene having at least three hydroxyl groups at the $R_1$–$R_5$ positions. The assay comprises the steps of removing at least one of the hydroxyl groups from the trichothecene (e.g. conversion to another group) to form a variant which has no greater than two hydroxyl groups at the $R_1$–$R_5$ positions, and then using an antibody capable of binding to the variant to test for the presence of the variant in the modified sample.

If one has first tested the original sample using that antibody (to determine a control level in the sample before the removal of the OH group), the test of the modified sample will provide a measure of the presence of multi-hydroxyl trichothecene. In the alternative, the antibody can act as a screen for the presence of any one of many trichothecenes (including the multi-hydroxyl one).

The preferred manner of removing the OH group(s) is to expose the trichothecene to acidic anhydride in the presence of pyridine or aminopyridine, which will convert the OH group(s) at the $R_1$–$R_5$ position to acetate groups. The preferred trichothecenes are DON (which has three hydroxyl groups), T-2 tetraol (which has four hydroxyl groups), and nivalenol (which has four hydroxyl groups). It is expected that the assay will also work with other hydroxylated trichothecenes that are currently not amenable to immunoassay techniques.

The nomenclature $R_1$, $R_2$, $R_3$, $R_4$, and $R_5$ is defined as shown in FIG. 1.

In another form, the invention comprises a kit with an antibody capable of binding to Tri—Ac—DON, and a radioactively labelled compound (e.g. tritiated Tri—Ac—DON) that the antibody also competitively binds to. Another kit can be provided in which the antibody is capable of binding to T-2 TA.

The manner of obtaining the antibodies is discussed in detail in the preferred embodiment section of this application. In short, the variant (e.g. in which the OH groups have been converted to acetate groups) is altered to create a reactive site and then conjugated to a protein such as BSA. The conjugate is then used to immunize a rabbit (or other animal) so as to produce the antibodies of interest. Using what have now become conventional techniques, monoclonal forms of the antibody can then be obtained.

An object of the invention therefore includes providing an immunoassay of the above kind in which trichothecenes having at least three hydroxyl groups can be assayed for.

Another object is to provide an assay of the above kind which is simple, relatively inexpensive, and easy to perform.

Another object is to provide kits for conducting assays of the above kind. Still other objects and advantages of the present invention will be apparent from the description which follows.

DESCRIPTION OF THE DRAWINGS

A better understanding of the present invention will be accomplished by reference to the drawings. It should be understood, however, that the drawings and the description of the preferred embodiments are merely examples of the invention. They are not intended to represent the full scope of the invention. Rather, the claims should be looked to in order to determine the full scope of the invention.

FIG. 1 depicts the basic chemical structure of trichothecenes, with the letters $R_1$, $R_2$, $R_3$, $R_4$, and $R_5$ designating substitution positions on the basic framework;

FIG. 2 is a chart describing some of the more common trichothecenes;

Figure 3:
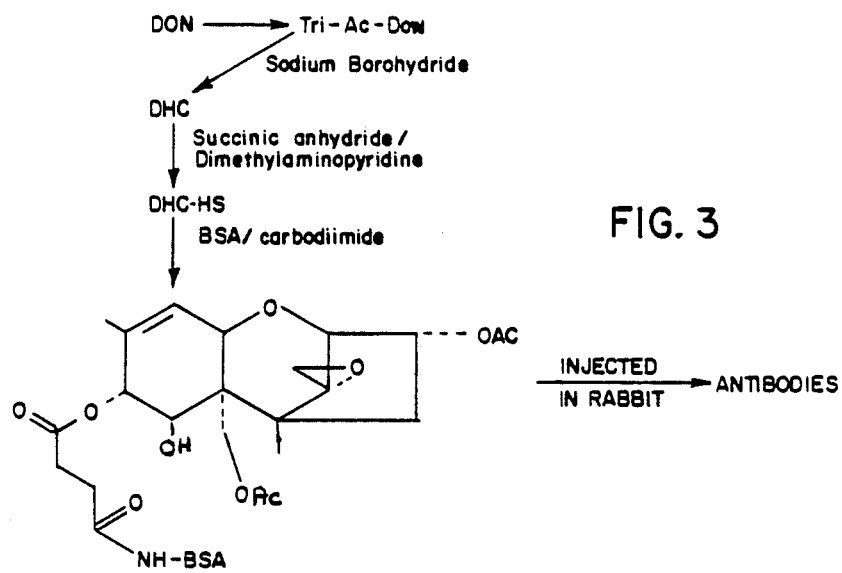
FIG. 3 is a schematic depiction of the chemistry involved in the development of the antibodies for the DON assay.

In the drawings, abbreviations are as follows: TA is tetra-acetate, OAc is $OCOCH_3$, ISV is $OCOCH_2CH(CH_3)_2$ and CMO is $=NOCH_2COOH$.

Description Of The Preferred Embodiments

Example 1 P DON Assay

Deoxynivalenol (DON) is one of the trichothecenes which causes feed refusal and other problems in swine. It is sometimes called "vomitoxin". FIG. 2 shows that DON has OH's at the $R_1$, $R_3$, and $R_4$ positions, and a $=O$ at $R_5$.

As shown in schematic form in FIG. 3, the approach involved for DON is to first obtain antibodies against Tri—Ac—DON. One does this by obtaining Tri—Ac—DON and then converting Tri—Ac—DON to 7,8-dihydroxycalonectrin (DHC) (see FIG. 2), a compound having OH at the $R_4$ and $R_5$ positions. This compound is then converted with a hemisuccinate group substituting for the OH at $R_5$. The resulting compound is then linked to bovine serum albumin (BSA) and injected into rabbits to form the antibody. A description in somewhat more detail of this technique is described in our article G. Zhang et al., 49 J. Fd. Prot. 336-339 (1986) (not prior art).

Materials And Methods

DON was produced by *Fusarium Graminearum* strain NRRL 5883 in cracked corn at 25° C. using the conditions described by R. Vesonder et al., 16 Process Biochem. 12-15 (1980). The toxin was extracted from the culture with methanol and purified on a silica gel column as described previously in G. Bennett et al., 58 J. Am. Oil Chem. Soc. 1002A-1005A (1981). Primary DON standard was provided by Northern Regional Research Center, U.S. Department Of Agriculture, Peoria, Ill.

DON—triacetate (Tri—Ac—DON) was prepared according to the method described previously. K. Ehrlich, 48 Microbiol. 1053-1054 (1984). Bovine serum albumin ("BSA"; RIA grade) was purchased from Sigma Chemical Co. (St. Louis, Mo.). Tritiated DON was prepared in a manner analogous to the method of making tritiated DOVE described in Chu et al, 48 Appl. Environ. Microbiol. 781-784 (1984). The basic technique is to selectively oxidize the $R_3$ hydroxyl group to =O at −20° C. for 30 minutes, and then to reduce the =O group with tritiated sodium borohydride at −20° C. for 30 minutes. Tritiated Tri—Ac—DON was prepared by acetylation of tritiated DON with acetic anhydride in the presence of pyridine. Water soluble carbodiimide, 1-ethyl-3,3-dimethylamino-propyl-carbodiimide (EDPC), was obtained from Aldrich Chemical Co. (Milwaukee, Wis.). Complete Freund's adjuvant containing *Mycobacterium tuberculosis* (H37 Ra) and incomplete Freund's adjuvant were obtained from Difco Laboratories (Detroit, Mich.). Albino female rabbits (2.27 kg) were purchased from Klubertanz Rabbit Farm (Edgerton, Wis.) and tested to be Pasteurella negative before use. All chemicals and organic solvents were reagent grade or better.

Preparation Of 7,8-Dihydroxycalonectrin ("DHC") And Hemisuccinate ("HS") Of DHC 7,8-Dihydroxycalonectrin was prepared by reduction of Tri—Ac—DON with sodium borohydride using the conditions described previously in F. Chu et al., 48 Appl. Environ. Microbiol. 781-84 (1984), and was purified by preparative TLC. Succinylation of DHC was achieved by reaction of DHC with succinic anhydride in the presence of dimethylaminopyridine under the conditions analogous to those described for diacetoxyscirpenol. F. Chu et al., 48 Appl. Environ. Microbiol. 777-780 (1984). The compound was isolated by preparative TLC.

Conjugation of DHC-HS to BSA was done in the presence of water soluble carbodiimide (EDPC) using procedures analogous to those described previously for T-2 toxin in F. Chu et al., 37 Appl. Environ. Microbiol. 104-108 (1979).

Production Of Antibody

Immunization schedule and methods of immunication were essentially the same as those described for T-2 toxin in F. Chu et al., 37 Appl. Environ. Microbiol. 104-108 (1979) using the multiple injection technique in three rabbits. The rabbits were each injected intradermally at multiple sites on the back with 2.0 μg of immunogen (DHS-HS-BSA) which was prepared by emulsifying 500 to 600 μg of the immunogen in 0.5 ml of sterilized phosphate-saline buffer (PBS, 0.1M sodium-phosphate buffer containing 0.9% NaCl, pH 7.5) with 1.5 ml of complete adjuvant.

Preimmune serum was obtained from each rabbit before immunization. Bleedings and booster injections were made at appropriate times after initial injection. For booster injection, 250 to 500 μg of antigen in 1.0 ml of PBS were emulsified with 1.0 ml incomplete adjuvant and were injected into the thigh. The collected antisera were precipitated with $(NH_4)_12SO_4$ to a final saturation of 33.3%. The precipitates were redissolved in water and reprecipitated two times. Finally, the precipitates were reconstituted to one-half of the original volume with 0.1M PBS, dialyzed against distilled water for 30 min., then against 0.01M phosphate buffer (pH 7.0) overnight at 6° C. and lyophilized.

Radio immunoassay ("RIA")

Basically, our RIA procedure involves incubation of specific antibody simultaneously with a solution of unknown sample or known standard, and a constant amount of a competing radioactively labelled toxin (usually a tritiated variant of the compound the antibody binds to). After separation (usually by precipitation) of the free from the bound toxin, the radioactivity in the respective fractions can then be determined. The toxin concentration of the unknown sample is determined by comparing the results to a standard curve. Several known methods, including the ammonium sulfate precipitation method, double antibody technique, a solid phase RIA method in which the immunoglobulin G (IgG) was conjugated to CNBr-activated sepharose gel, a dextrancoated charcoal column and albumin-coated charcoal, have been used for the separation of free and bound trichothecene toxins in RIA.

A preferred protocol for Tri—Ac—DON is analogous to that described for T-2 toxin, in which an ammonium precipitation method was used to separate the free and bound toxin. F. Chu et al., 37 Appl. Environ. Microbiol. 104–108 (1979). In general, 50 µl of radioactive Tri—Ac—DON (10,000 to 15,000 dpm) (the "hot" competitive compound) was incubated with 0.15 ml of antibody solution of various dilutions in phosphate buffer (0.1M, pH 7.2) at room temperature for 30 min., and then in a cold room (6° C.) overnight. Separation of the bound and free ligand was achieved by an ammo ammonium sulfate precipitation method as described in the Chu article. Radioactivity was determined in a Beckman model LS-5800 liquid scintillation spectrometer in 5 ml of Aquasol (New England Nuclear Corp., Boston, Mass.) for aqueous solution. It might be noted that the resulting antibody recognized several other trichothecenes besides just Tri—Ac—DON.

RIA Assay For Natural Samples

With the availability of antibody against DON-triacetate, a radio immunoassay for DON in natural wheat was developed. DON is extracted from the wheat sample with acetonitrile-water (84+16), defatted with hexane, and then reacted with acetic anhydride in pyridine to form DON-triacetate. The reaction mixture is loaded onto a C-18 cartridge to remove excess reagents and impurities. Acetylated DON is eluted from the cartridge with 50% methanol in water, and then analyzed by radio immunoassay utilizing antiserum against DON-triacetate and tritiated DON-triacetate. The limit of detection of DON was about 20 ppb. Analysis of twelve naturally contaminated wheat, corn, and mixed feed samples for DON revealed that RIA results agreed well with thin layer chromatographic analyses. For greater detail on this see our article see our article. Xu et al., 69 J. Assoc. Off. Anal. Chem. 967–969 (1986) (not prior art). The assay will also show positive if mono-acetyl DON or biacetyl DON was in the original sample.

ELISA Assay

Two types of ELISA assays (namely direct and indirect) have been used for analysis of some trichothecenes. See generally F. Chu, Mycotoxins And Phycotoxins (1986); F. Chu, 47 J. Fd. Prot. 562–569 (1984). Although both types are competitive assays, the direct type ELISA uses a toxinenzyme conjugate as a marker as compared to the indirect system, in which a protein-toxin conjugate and a secondary antibody to which the enzyme has been conjugated, are used.

Direct Competitive ELISA

Horseradiah peroxidase (HRP) can be the enzyme conjugated with mycotoxins in the direct system. The antibodies are first coated to a solid phase, most commonly to the wells of a micrometer plate. The sample solution or standard toxin is then incubated with enzyme-toxin conjugate in the antibody-coated microplate wells. After appropriate washings, the amount of enzyme remaining bound to the plate is then determined by incubation with a substrate solution containing hydrogen peroxide and appropriate oxidizable chromogens. The resulting color is then measured spectrophotometrically or by visual comparison with the standards. Because of the competition of binding between free toxin and the enzyme-toxin conjugate with the antibody in the microplate well, the presence of toxin in the sample results in a decrease in enzyme concentration, and subsequently yields less color.

Indirect Competitive ELISA

In the indirect ELISA, instead of using the toxin-enzyme conjugate, which may be prone to enzyme stability problems, a toxin-protein (or polypeptide) conjugate is first prepared and then coated to the microplate before assay. The plate is then incubated with specific rabbit antibody in the presence or absence of the homologous toxin. The amount of antibody bound to the plate coated with toxin-protein conjugate is then determined by reaction with goat anti-rabbit IgG-enzyme complex, which is generally commercially available, and by subsequent reaction with the substrate. Thus, the protein-toxin coated to the plate competes with the free toxin in their binding with the anti-toxin antibody, and the secondary anti-IgG-enzyme conjugate is used as the marker. Both HRP and alkaline phosphates conjugated to the goat anti-rabbit-IgG have been used.

EXAMPLE 2

Figure 4:
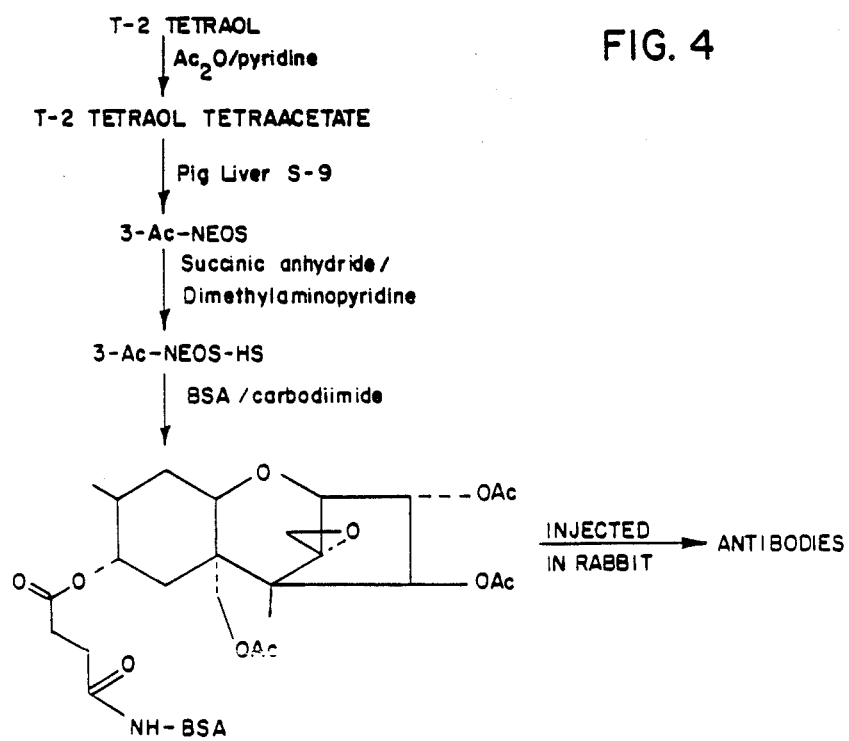
FIG. 4 is a schematic view of the chemistry involved in the development of antibodies for the T-2 tetraol assay.

Our techniques for converting T-2 tetraol to T-2 tetra acetate, and then forming antibodies to the resultant product are described in Wei et al., 160 Anal. Biochem. 399–408 (1987) (not prior art). The overall approach is schematically depicted in FIG. 4.

Synthesis Of T-2 Tetraol Tetraacetate

The first step is to convert all T-2 tetraol OH groups in the $R_1$–$R_5$ positions to OAC. A mixture of 66 mg of T-22 tetraol, 3 ml of dry pyridine, and 3 ml of acetic anhydride was placed in a bottle with a stopper at room temperature for 2 h. Five milliliters of ethanol were added to the reaction mixture and the solution was evaporated in vacuo to an oily product which was then dissolved in 3 ml of ethyl acetate and chromatographed on a column (1×19 cm) packed with 7 g of silica gel G-60 (mesh 70–230, Merck AG, Darmstadt, FRG) and n-hexane.

The column was washed with 50 ml of n-hexane and then eluted with 100 ml of n-hexane-ethyl acetate (50:50, vol/vol). The eluate from 15th to 80th ml which showed a single spot in thin-layer chromatography was pooled and concentrated in vacuo to a glassy solid that simultaneously crystallized. The colorless crystals weighed 88 mg, mp 177°–178° C.

Enzymatic Hydrolysis Of T-2 Tetraol Tetraacetate To 3-Acetylneosolaniol (3-AC-NEOS)

The next step is to change the $R_5$ OAC to OH to provide a linker site. T-2 tetraol tetra-acetate was selectively hydrolyzed to 3-Ac-NEOS with pig liver S-9 according to the method of Yoshizawa et al., 46 Agric. Biol. Chem. 2613–2615(1982), except that the S-9 was prepared in a 0.25 M sodium phosphate buffer (NaPB), pH 7.4, instead of Tris-HCl buffer. In a 500-ml Erlenmeyer flask, 88 mg of T-2 tetraol tetraacetate crystals were moistened with 1 ml of dimethylsulfoxide followed by addition of 6 ml of ethanol and shaking at 37° C. to dissolve the crystals. After adding 120 ml of pig liver S-9, the mixture was incubated with shaking at 37° C. for 1 h. and the reaction was terminated by directly applying the reaction mixture to an Amberlite XAD-2 column (1.9×19 cm).

After washing with 300 ml of distilled water, the metabolites were eluted from the column with 150 ml of acetone. The acetone eluate was rotary evaporated to a few milliliters. Distilled water (10 ml) was added to the residue, which was then extracted with four 20-ml portions of $CHCl_3$. The combined $CHCl_3$ extract was concentrated in a rotary evaporator to an oily product, which was subsequently redissolved in a small amount of $CHCl_3$ and chromatographed on a column (1×14 cm) packed with 6 g of Florisil and equilibrated with $CHCl_3$. Stepwise elution with 30 ml of $CHCl_3$ and 25 ml each of 1, 2, and 3% MeOH in $CHCL_3$ was performed. The eluate with 2% MeOH in $CHCl_3$ gave a single spot in thin-layer chromatography with a $R_f$ value of 0.44 in chloroform:acetone (3:2, vol/vol) compared with the starting T-2 tetraol tetra-acetate, which had had a $R_f$ of 0.63. This fraction weighed 57 mg after it was evaporated to dryness.

Preparation Of Hemisuccinate Of 3—Ac—NEOS

The OH at $R_5$ is then used to add a linker. A hemisuccinate of 3—Ac—NEOS was prepared by procedures analogous to those previously described for the preparation of T—2—HS in Chu et al., 37 Appl. Environ. Micro. 104–108 (1979). Briefly, 20 mg of 3—Ac—NEOS and 10 mg of 4-dimethylaminopyridine were dissolved in 1.3 ml of dry tetrahydrofuran. Succinic anhydride (30 mg each) was added to the reaction mixture in the beginning of the experiment and then every 30 min during a reflux period of 3 h. Thin-layer chromatography revealed that almost all of the 3—Ac—NEOS was converted to a new product. The reaction mixture was evaporated to dryness under nitrogen, redissolved in $CHCl_3$, and washed with 0.1 N HCl and then distilled water. The combined $CHCl_3$ extracts were rotary evaporated to dryness, redissolved in a small amount of $CHCl_3$ and chromatographed on a column (1×12 cm) packed with 5.3 g of Florisil and equilibrated with n-hexane. The column was stepwise eluted with 20 ml each of n-hexane, n-hexane:ethyl acetate (3:1, vol/vol), n-hexane: ethyl acetate:glacial acetic acid (40:60:1, vol/vol/vol) and ethyl acetate:glacial acetic acid (99:1, vol/vol). The eluate with the last two solvents gave a single spot in thin-layer chromatography with a $R_f$ value of 0.59 in ethyl acetate:MeOH:glacial acetic acid (88:10:2, vol/vol/vol). The product was confirmed to be 3—Ac—NEOS—HS by mass spectral analysis.

The HS group is then linked to bovine serum albumin. Conjugation of 3—Ac—NEOS—HS to BSA was carried out in the presence of a water soluble carbodiimide (EDPC) using procedures analogous to those previously described for T-2 toxin in Chu et al., 37 Appl. Environ. Microbiol. 104–108 (1979).

Production Of Antibody

Antibody to the conjugate was then produced. The immunization schedule and methods of immunization were analogous to those described for T-2 toxin Chu et al., 37 Appl. Environ. Microbiol. 104–108 (1979). Five rabbits were used. Each rabbit was injected intradermally with 500 μg of the immunogen (3—Ac—NEOS—HS—BSA) in 1.0 ml of 0.1 M sodium phosphate buffer (pH 7.4) containing 0.85% NaCl (PBS), with 2.0 ml of complete Freund's adjuvant. For booster injections, 500 μg of antigen in 1.0 ml of PBS and 2.0 ml incomplete Freund's adjuvant was used. The collected antisera were precipitated with $(NH_4)_2SO_4$ to a final saturation of 33.3%. The precipitates were redissolved in water and reprecipitated twice. Finally, the precipitates were reconstituted to half of the original volume with distilled water, dialyzed against distilled water for 0.5 to 1 h, then against 0.01 M PBS overnight at 6° C., and then lyophilized.

Radioimmunoassay

Protocols for the assay were essentially the same as those described for T-2 toxin in which an ammonium sulfate precipitation method was used to separate free and bound toxin. 3H—T—2 (tritiated) tetraol tetraacetate was used as the marker ligand. It is prepared from tritiated T-2 tetraol by acetylation. Tritiated T-2 tetraol was prepared by hydrolysis of tritiated T-2. See Wei et al., 45 Biochem. Biophys. Res. Comm. 396–401 (1971). Tritiated T-2 was made as described in Wallace et al., 25 J. Ag. Fd. Chem. 836–838 (1977). 50 μl of radioactive marker ligand (10,000 to 12,000 dpm) was incubated with 0.15 ml of antiserum solution of various dilutions in PBS at room temperature for 30 min and then in a cold room (6° C.) for 1 h or longer. Separation of bound and free ligand was achieved by the ammonium sulfate precipitation method described earlier Chu et al., 37 Appl. Environ. Microbiol. 104–108 (1979).

Radioimmunoassay Of Toxin In Corn

An appropriate amount of pure T-2 tetraol in acetone was mixed with white corn meal (Quaker) to final concentrations of 10, 20, and 50 ppb. The samples were dried at room temperature overnight to remove the acetone, and then subjected to extraction and cleanup. For each analysis, 1 g of sample in a 16×100-mm screw-capped test tube was mixed with 5 ml of acetone in a Vortex Genie Mixer for 5 min and then centrifuged. After centrifugation, 3 ml of the supernatant was transferred to a vial to which 12 ml of distilled water was added. The 20% acetone extract (total 15 ml) was then passed through a Sep-Pak C-18 reversed-phase cartridge which had been previously washed with 5 ml of acetone and then 20 ml of distilled water. After washing with 10 ml of 20% aqueous acetone (washing discarded), the toxin was eluted from the cartridge with 2.4 ml of 60% aqueous acetone. The eluates were diluted at least 10 times with PBS and subjected to RIA. The assay will also show positive if T-2, H-T2, T-2 triol, 3'OH-T-2, or DAS is in the original sample.

EXAMPLE 3

Another part of our work is described in T. Fan et al., 53 Appl. Environ. Microbiol. 17–21 (1987) (not prior art) where we describe means for preparing an antibody to CMO—T—2—4Ac (CMO is where $R_1$ is the linker $=N-O-CH_2-CO_2H$). This antibody also recognizes T—2—4—Ac and again permits one to assay for T-2 tetraol by converting it to T—2—4—Ac with acetic anhydride in pyridine.

EXAMPLE 4

Monoclonal Techniques

A monoclonal antibody assay (as opposed to the above described polyclonal assays) can be developed. For example, a monoclonal antibody against T-2 toxin has been produced by fusion of P3-NS1/1-Aq4-1 myeloma cells with spleen cells of a BALB/c mouse which had been immunized with 3-acetyl-neosolaniol, a derivative of T-2 tetraol tetraacetate, conjugated to BSA. A radioimmunoassay, using tritiated T-2 toxin and diacetoxyscirpenol (DAS) as marker ligands, was used in screening the hybrid cells. One stable clone which produced antibody bound with both T-2 toxin and DAS was obtained after screening and subcloning. Similar selection techniques should permit identification and development of other monoclonals.

As can be seen from these examples, the problem in the art is solved by removing (e.g. converting) interfering OH groups, and developing antibodies for the variant trichothecenes so created. Some of the antibodies so created will have broad trichothecene specificity, thus permitting one to at the same time test for the presence of other trichothecenes as well.

Since OH to OAC conversions of trichothecenes are readily accomplished without affecting other immuno important groups, it is the preferred "removal" technique. However, still other removal techniques may also prove successful (e.g. substituting benzyl groups). Further, removal of all OH groups at $R_1$–$R_5$ is not always required. It is expected that good results can be achieved when less than three OH remain at $R_1$–$R_5$ positions on the variant.

Moreover, while DON and T-2 tetraol are specifically discussed herein, it should be appreciated that other trichothecenes having at least three hydroxyl groups should be amenable to these techniques. Further, the term "trichothecene" is used herein in its broadest sense (e.g. covering not only natural compounds, but also man-made variants).

We claim:

1. An assay for the presence in a sample of a trichothecene having at least three hydroxyl groups at the $R_1$–$R_5$ positions, the trichothecene having the formula:

the assay comprising the steps of:
 converting a hydroxyl group of the trichothecene to an organic moiety linked to the remainder of the trichothecene by oxygen, so as to form a variant with no more than two hydroxyl groups at the $R_1$–$R_5$ positions; and
 adding an antibody capable of binding to the variant j and determining the presence of said trichothecene in said sample as a measure of said antibody binding to said variant.

2. The assay of claim 1, comprising the further step of:
 first testing the sample using said antibody to determine a control level in the original sample.

3. The assay of claim 1, wherein an OH group is converted to an ester in the variant.

4. The assay of claim 1, wherein a OH group is converted to OAC in the variant.

5. The assay of claim 1, wherein the trichothecene is deoxynivalenol.

6. The assay of claim 1, wherein the trichothecene is T-2 tetraol.

7. The assay of claim 1, wherein the trichothecene is nivalenol.

* * * * *

UNITED STATES PATENT AND TRADEMARK OFFICE
CERTIFICATE OF CORRECTION

PATENT NO. : 4,879,248

DATED : November 7, 1989

INVENTOR(S) : Fun S. Chu; Ru-Dong Wei; Guang S. Zhang

It is certified that error appears in the above-identified patent and that said Letters Patent is hereby corrected as shown below:

On the title page:

| | |
|---|---|
| References Cited, line 21 | "Vleggar" should read --Vleggaar-- |
| Column 3, line 29 | "1 P DON" should read --1 - DON-- |
| Column 4, line 56 | "$(NH_4)_1 2SO_4$" should read --$(NH_4)_2 SO_4$-- |
| Column 6, line 1 | "micrometer" should read --microtiter-- |
| Column 6, lines 31 and 32 | "phos-phates" should read --phosphatase-- |
| Column 8, line 21 | "3H-T-2" should read --$^3$H-T-2-- |
| Column 8, line 67 | "T-2-4-Ac" should read --T-2-4Ac-- |
| Column 10, line 24 | "variant" should read --variant; and-- |

UNITED STATES PATENT AND TRADEMARK OFFICE
CERTIFICATE OF CORRECTION

PATENT NO. : 4,879,248

DATED : November 7, 1989

INVENTOR(S) : Fun S. Chu, et al

It is certified that error appears in the above-identified patent and that said Letters Patent is hereby corrected as shown below:

Column 10, line 25            "j and" should be deleted.

Signed and Sealed this

Twenty-fifth Day of September, 1990

Attest:

HARRY F. MANBECK, JR.

*Attesting Officer*      *Commissioner of Patents and Trademarks*